(12) United States Patent
Näsholm et al.

(10) Patent No.: US 7,741,540 B2
(45) Date of Patent: *Jun. 22, 2010

(54) COMPOSITIONS COMPRISING D-AMINO ACIDS

(75) Inventors: Torgny Näsholm, Holmsund (SE); Oskar Erikson, Umea (SE); Magnus Hertzberg, Umea (SE)

(73) Assignees: BASF Plant Science GmbH (DE); SweTree Technologies AB (SE)

( * ) Notice: Subject to any disclaimer, the term of this patent is extended or adjusted under 35 U.S.C. 154(b) by 63 days.

This patent is subject to a terminal disclaimer.

(21) Appl. No.: 11/473,552

(22) Filed: Jun. 23, 2006

(65) Prior Publication Data

US 2007/0016973 A1 Jan. 18, 2007

Related U.S. Application Data

(62) Division of application No. 10/500,377, filed as application No. PCT/EP03/00222 on Jan. 13, 2003, now Pat. No. 7,105,349.

(30) Foreign Application Priority Data

Jan. 17, 2002 (GB) .................................. 0201043.7

(51) Int. Cl.
*A01H 5/00* (2006.01)
*A01H 1/04* (2006.01)
*C12N 15/82* (2006.01)

(52) U.S. Cl. ........................................ 800/300; 800/288
(58) Field of Classification Search ........................ None
See application file for complete search history.

(56) References Cited

U.S. PATENT DOCUMENTS

| | | | |
|---|---|---|---|
| 4,714,196 A * | 12/1987 | McEachern et al. | 239/62 |
| 5,463,175 A | 10/1995 | Barry et al. | |
| 5,877,013 A | 3/1999 | Liao et al. | |
| 5,948,660 A | 9/1999 | Pilone | |
| 6,187,574 B1 | 2/2001 | Lopez et al. | |
| 7,105,349 B2 * | 9/2006 | Nasholm et al. | 435/468 |

OTHER PUBLICATIONS

Janzen et al. Compost extract added to microcosms may simulate community-level controls on soil microorganisms involved in element cycling. (1995) Soil Biol. Biochem.; vol. 27, pp. 181-188.*
Huffman and Ingersoll; The resolution of amino acids. II. Isoleucine, alloisoleucine, leucine, and norleucine. (1951) J. ACS; vol. 73, pp. 3366-3369.*
Kopple et al. Solution conformation of a retro-D analogue of Tocinamide. (1976) Biochemistry; vol. 15, pp. 2945-2952.*
Hitz et al. Stereoselectivity aspects in the condensation of racemic NCA-amino acids in the presence and absence of liposomes. (2001) Macromolecules; vol. 34, pp. 2443-2449.*

Eghball et al. Phosphorus- and Nitrogen-Based Manure and Compost Applications: Corn Production and Soil Phosphorus. (1999) Soil Sci. Soc. Am. J.; Bol. 63; pp. 895-901.*
Dalton et al. The solubilities of certain amino acids and related compounds in water, the densities of their solutions at twent-five degrees, and the calculated heats of solution and partial molal vols. II (1934) JBC; vol. 109; pp. 241-248.*
Lehninger, et al., Principles of Biochemistry, Second Edition (1993), Worth Publishers, New York.
Database Accession No. AC006340 (XP002250252), positions 35204-37432.
Robinson, Trevor, "D-Amino Acids in Higher Plants," Life Sciences (1976), vol. 19, No. 8, pp. 1097-1102.
Guo, Lining et al., "Amino Acid N-Malonyltransferases from Mung Beans," Journal of Biological Chemistry (1993), vol. 268, No. 34, pp. 25389-25394.
Ogawa, Tadashi et al., "Occurrence of D-Amino Acid Aminotransferase in Pea Seedlings," Biochemical and Biophysical Research Communications (1973), Academic Press, San Diego, CA, vol. 52, No. 3, pp. 998-1002.
Koshiba, Tomokazu et al., "L- and D-Tryptophan Aminotransferases from Maize Coleoptiles," Journal of Plant Research (1993), vol. 106, No. 1081, pp. 25-29.
Rekoslavskaya, N. I., et al., "D-Tryptophan as IAA Source During Wheat Germination," Bulgarian Journal of Plant Physiology (1999), vol. 25, No. 1-2, pp. 39-48.
Lipson, David, et al., "The Unexpected Versability of Plants: Organic Nitrogen Use and Availability in Terrestrial Ecosystems," Oecologia (Berlin) (2001), vol. 128, No. 3, pp. 305-316.
Nasholm Torgny, et al., "Boreal Forest Plants Take Up Organic Nitrogen," Nature (1998), vol. 392, pp. 914-916.
Nasholm, Torgny, et al., "Uptake of Organic Nitrogen in the Field by Four Agriculturally Important Plant Species," Ecology (2000), vol. 81, No. 4, pp. 1155-1161.

(Continued)

*Primary Examiner*—Cathy Kingdon Worley
(74) *Attorney, Agent, or Firm*—Connolly Bove Lodge & Hutz LLP

(57) ABSTRACT

This invention relates to fertilizer and herbicide compositions. The present invention provides a composition for selective fertilization of a transgenic plant comprising a polypeptide which metabolizes a D-amino acid substrate; said composition comprising said D-amino acid substrate. Another aspect of the present invention provides a selective herbicide composition comprising a D-amino acid. Such a herbicide will inhibit or reduce the growth of plants which do not contain the appropriate D-amino acid metabolizing enzyme, while the growth of transgenic plants which are able to metabolize the D-amino acid will be unaffected or, more preferably, be increased or enhanced. Methods and means are also provided for selectively modulating the growth and stress tolerance such plants using D-amino acids. The methods can be used either for detoxification of phytotoxic D-amino acids such as D-alanine and D-serine, thereby allowing for selection of plants comprising said D-amino acid metabolizing enzymes, or for enhancing toxicity of lesser phytotoxic D-amino acids such as D-isoleucine, thereby allowing for selection of plants not comprising said D-amino acid metabolizing enzymes.

7 Claims, 5 Drawing Sheets

OTHER PUBLICATIONS

Nasholm, Torgny, et al., "Plant Acquisition of Organic Nitrogen in Boreal Forests," Physiol. Plant (2001), vol. 111, pp. 419-426.

Lipson, David et al., "The Unexpected Versatility of Plants: Organic Nitrogen Use and Availability in Terrestrial Ecosystems," Oecologia (2001), vol. 128, pp. 305-316.

Soldal, Trond, et al., "Multiphasic Uptake of Amino Acids by Barley Roots," Physiol. Plant (1978), vol. 43, pp. 181-188.

Boorer, Kathryn J., et al., "Kinetics and Specificity of a H+/Amino Acid Transporter from *Arabidopsis thaliana*," J. Biol. Chem. (1996), vol. 271, No. 4, pp. 2213-2220.

Montamat, Florence, et al., "Cloning and Expression of Amino Acid Transporters from Broad Bean," Plant Molecular Biology (1999), vol. 41, pp. 259-268.

Friedman, Mendel, "Chemistry, Nutrition, and Microbiology of D-Amino Acids," J. Agric. Food Chem. (1999), vol. 47, No. 9, pp. 3457-3479.

Pilone, M.S., "D-Amino Acid Oxidase: New Findings," Cell Mol. Life Sci. (2000), vol. 57, pp. 1732-1747.

Yurimoto, Hiroya et al., "Physiological Role of the D-Amino Acid Oxidase Gene, DAO1, in Carbon and Nitrogen Metabolism in the Methylotrophic Yeast *Candida boidinii*,", Yeast (2000), vol. 16, pp. 1217-1227.

GenBank: NCBI accession No. J01603.
GenBank: NCBI accession No. U60066.
GenBank: NCBI accession No. AAC76949.

* cited by examiner under 35 U.S.C. 371) of PCT/EP2003/00222 filed Jan. 13, 2003 which claims benefit to U.K. application 0201043.7 filed Jan. 17, 2002.

US 7,741,540 B2

COMPOSITIONS COMPRISING D-AMINO ACIDS

CROSS-REFERENCE TO RELATED APPLICATION

The present application is a division of application Ser. No. 10/500,377, filed Jun. 30, 2004 now issued as U.S. Pat. No. 7,105,349 on Sep. 12, 2006, which is hereby incorporated by reference in its entirety, which is a national stage application (under 35 U.S.C. 371) of PCT/EP2003/00222 filed Jan. 13, 2003 which claims benefit to U.K. application 0201043.7 filed Jan. 17, 2002.

FIELD OF THE INVENTION

The present invention relates to the selective growth of plant cells, plant tissue or vascular plants containing foreign genetic material.

BACKGROUND OF THE INVENTION

Nitrogen is needed in large amounts by plants as a mineral nutrient. Plant growth, particularly in agriculture, is often limited by the amount of available nitrogen.

Traditionally, plants have been considered to use only ammonium and/or nitrate as sources of nitrogen. These compounds are supplied either by natural processes, such as the mineralisation of organic nitrogen and nitrogen fixation by symbiotic prokaryotes, or by the application of fertilisers containing industrially fixed nitrogen.

However, recent research has indicated that plants may also have access to certain organic nitrogen compounds, as well as inorganic nitrogen (Näsholm, T. et al. (1998) Nature 392, 914-916, Näsholm, T. et al (2000) Ecology 81: 1155-1161, Näsholm, T. and Persson, J. (2001) Physiol Plant 111: 419-426, Lipson, D. and Näsholm, T. (2001) Oecologia 128: 305-316). In particular, the uptake and metabolism of amino acids from soil seems to be a ubiquitous feature of plants.

Among the amino acids used as building blocks for proteins, all but one (glycine) can be found in two isomeric forms which are distinguished by their ability to rotate polarised light. The form found in largest quantities in nature rotates light to the left and is termed L- or levorotatory, while the less common form is termed D- or dextrorotatory.

Whilst D-amino acids are found in nature, they are present only at very low concentrations and only in specific compounds as cell wall proteins in bacteria (e.g. in the compound peptidoglucan).

Although plant amino acid transporters mediate transport of both D- and L-forms of amino acids (Soldal, T. and Nissen, P. (1978) Physiol. Plant. 43: 181-188, Boorer, K. J. et al. 1996. J. Biol. Chem 271: 2213-2220, Montamat et al (1999) Plant Mol. Biol. 41: 259-268), plants lack the necessary enzymes to convert D-amino acids into nitrogen forms that can be used in synthetic reactions inside the plant. Plants cannot therefore use D-amino acids as a source of nitrogen.

The capacity to metabolise D-amino acids is, however, widespread among bacteria, fungi and animals. Several reactions have been described, leading to catabolism of D-amino acids in organisms (see FIG. 2) (Friedman, M (1999) J. Agric. Food Chem. 47: 3457-3479, Pilone, M. S. (2000) CMLS 57: 1732-1747, Yurimoto et al. (2000) Yeast 16(13): 1217-1227).

SUMMARY OF THE INVENTION

The present inventors have discovered that plants which express a heterologous gene encoding an enzyme that metabolises a D-amino acid are able to utilise that D-amino acid as a nitrogen source and grow on media which would not otherwise support growth of the wild-type plant.

DETAILED DESCRIPTION

Figure 1:
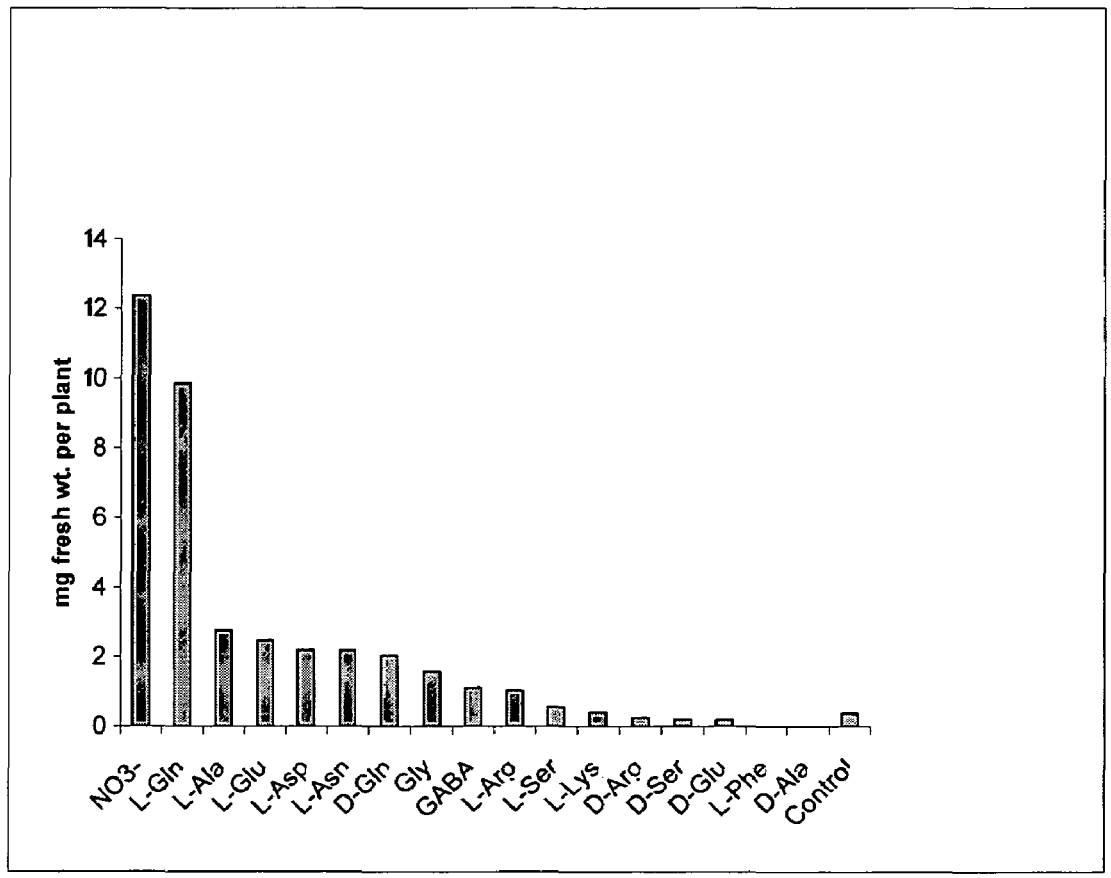
FIG. 1. Fresh weight of *Arabidopsis thaliana* plants grown for 20 days in sterile agar culture supplied with different nitrogen sources.

Generally, only a single D-amino acid metabolising enzyme is needed to convert the D-amino acid into compounds that can participate in the usual plant pathways of nitrogen metabolism (i.e. compounds which are non-dextrorotatory). For example, the enzyme D-serine dehydratase may be used to convert D-serine into ammonia, pyruvate and water and D-amino acid oxidases may be used to convert D-amino acids into ammonia, a keto acid (depending on the D-amino acid substrate) and hydrogen peroxide. Nitrogen that is otherwise inaccessibly bound in D-amino acids can thus be converted enzymatically into forms that can be readily utilised by the plant.

One aspect of the present invention provides an isolated nucleic acid comprising a sequence encoding a polypeptide which has D-amino acid metabolising activity, the sequence being operably linked to one or more plant specific regulatory elements.

In some embodiments of the invention, an isolated nucleic acid may consist of a sequence encoding a polypeptide which has D-amino acid metabolising activity and one or more plant specific regulatory elements operably linked to the sequence.

In some embodiments, D-amino acids may be used as selection markers. An isolated nucleic acid as described above may further comprise a heterologous nucleic acid sequence which encodes a polypeptide of interest. Expression of this polypeptide may, for example, alter the phenotype of a plant in an advantageous manner or produce other beneficial effects. Expression of the polypeptide with D-amino acid metabolising activity allows for the efficient selection of transformants which contain this heterologous nucleic acid sequence, as described herein.

A polypeptide which has a D-amino acid metabolising activity means a polypeptide which converts a D-amino acid substrate into products which are substrates for endogenous plant enzymes (i.e. they can be metabolised by plants). Products which are metabolised by plants include non-dextrotatory compounds i.e. non-chiral or L-compounds. The D-amino acid metabolising polypeptide therefore catalyses the biochemical conversion of a D-amino acid substrate into products, for example non-dextrotatory products, which may be used by plants as sources of nutrients, in particular as sources of nitrogen.

A suitable D-amino acid metabolising polypeptide may be a eukaryotic enzyme, for example from a yeast (e.g. *Rhodotorula gracilis*), fungus, or animal or it may be a prokaryotic enzyme, for example, from a bacterium such as *Escherichia coli*. Examples of suitable polypeptides which metabolise D-amino acids are shown in Table 1 and Table 2.

As described above, no endogenous D-amino acid metabolising activity has been reported in plants.

The substrate for the D-amino acid metabolising polypeptide may be D-arg, D-glu, D-ala, D-asp, D-cys, D-gln, D-his, D-ile, D-leu, D-lys, D-met, D-asn, D-phe, D-pro, D-ser, D-thr, D-trp, D-tyr or D-val.

Other suitable substrates for D-amino acid metabolising enzymes include non-protein dextrotatory amino acids, precursors of dextrotatory amino acids and dextrotatory amino acid derivatives. Such substrates may be used as a plant nitrogen source only after conversion into a suitable metabolisable form by a D-amino acid metabolising enzyme. Suitable precursors include D-ornithine and D-citrulline.

Preferably, the substrate for the D-amino acid metabolising polypeptide is one of D-ser, D-asn, D-ala, D-ile, D-glu, D-arg, D-lys, D-his or D-asp, more preferably D-ala, D-ile or D-ser.

The presence of a non-chiral amide group in a D-amino acid may produce small amounts of plant growth, as this group can often be metabolised by a plant and used as a source of nitrogen. For example, on medium containing D-gln, endogenous glutamate synthases act on the non-chiral amide group to generate D-glu. As the products of such non-chiral activity are other D-amino compounds which are not themselves metabolised by endogenous plant enzymes, growth rates with these D-amino acids are low, even though some nitrogen is made available.

The D-amino acid metabolising polypeptide may, for example, be an oxidase, racemase, decarboxylase, transaminase or dehydratase (also called an ammonia lyase). Oxidases catalyse the conversion of a D-amino acid into $NH_4^+$, a keto acid (depending on the D-amino acid substrate) and $H_2O_2$ (see FIG. 2). Racemases convert a D-amino acid into the corresponding L-amino acid form. L-amino acids are useful as a nitrogen source for plants. Decarboxylases convert a D-amino acid into a γ-amino acid which can be metabolised by plants. Transaminases convert a D-amino acid into a different L or D amino acid form. L-amino acids can then be metabolised directly whilst D-amino acids can undergo further conversion into metabolisable forms. Dehydratases catalyse the conversion of a D-amino acid into $NH_4^+$, a keto acid (depending on the D-amino acid substrate) and $H_2O$ (see FIG. 2). Examples of suitable oxidases, racemases, decarboxylases, transaminases and dehydratases are shown in Table 1 and Table 2.

In preferred embodiments, the D-amino acid metabolising polypeptide is a dehydratase, for example D-ser ammonia lyase (formerly known as D-ser dehydratase) or an oxidase, for example D-amino acid oxidase.

A skilled person is readily able to determine using routine techniques whether a polypeptide possesses a D-amino acid metabolising activity (i.e. is a D-amino acid metabolising enzyme), as described above.

Suitable D-amino acid metabolising polypeptides also include fragments, mutants, derivatives, variants and alleles of the polypeptides exemplified in Table 1 and Table 2.

Suitable fragments, mutants, derivatives, variants and alleles are those which retain the functional characteristics of the D-amino acid metabolising polypeptide i.e. which catalyse the reaction of a D-amino acid substrate into a plant-metabolisable form. Changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid that make no difference to the encoded amino acid sequence are included.

A polypeptide which metabolises a D-amino acid substrate may comprise an amino acid sequence which shares greater than about 30% sequence identity with a sequence shown in Table 1 or Table 2, greater than about 35%, greater than about 40%, greater than about 45%, greater than about 55%, greater than about 65%, greater than about 70%, greater than about 80%, greater than about 90% or greater than about 95%. The sequence may share greater than about 30% similarity with a sequence shown in Table 1 or Table 2, greater than about 40% similarity, greater than about 50% similarity, greater than about 60% similarity, greater than about 70% similarity, greater than about 80% similarity or greater than about 90% similarity.

Sequence similarity and identity is commonly defined with reference to the algorithm GAP (Genetics Computer Group, Madison, Wis.). GAP uses the Needleman and Wunsch algorithm to align two complete sequences that maximizes the number of matches and minimizes the number of gaps. Generally, default parameters are used, with a gap creation penalty=12 and gap extension penalty=4.

Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm (Nucl. Acids Res. (1997) 25: 3389-3402) may be used.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from a known polypeptide sequence as described herein by insertion, addition, substitution or deletion of 1 amino acid, 2, 3, 4, 5-10, 10-20 20-30, 30-50, or more than 50 amino acids.

A plant specific regulatory sequence or element is a sequence which preferentially directs the expression (i.e. transcription) of a nucleic acid within a plant cell relative to other cell types.

For example, expression from such a sequence may be reduced or abolished in non-plant cells, such as bacterial or mammalian cells. A suitable regulatory sequence may, for example, be derived from a plant virus such as Cauliflower Mosaic Virus 35.

A regulatory sequence is preferably heterologous or foreign to the gene encoding the D-amino acid metabolising enzyme. Such regulatory sequences may provide for efficient expression within a plant cell.

The term "heterologous" may be used to indicate that the gene/sequence of nucleotides in question have been introduced into said cells of the plant or an ancestor thereof, using genetic engineering or recombinant means, i.e. by human intervention.

Nucleotide sequences heterologous, or exogenous or foreign, to a plant cell may be non-naturally occurring in cells of that type, variety or species. For example, there are no reports of D-amino acid metabolising enzymes (i.e. enzymes which convert D-amino acids into plant-metabolisable forms) in plant cells and nucleic acid encoding a polypeptide with this activity is therefore "heterologous" to a plant cell transformed therewith.

In addition to regulatory sequences which are heterologous to the gene encoding the D-amino acid metabolising polypeptide, a nucleic acid may comprise one or more cis-elements from the endogenous promoter of the D-amino acid metabolising polypeptide.

By "promoter" is meant a sequence of nucleotides from which transcription of DNA operably linked downstream (i.e. in the 3' direction on the sense strand of double-stranded DNA) may be initiated.

"Operably linked" means joined as part of the same nucleic acid molecule, suitably positioned and oriented for transcription to be initiated from the promoter. DNA operably linked to a promoter is "under transcriptional initiation regulation" of the promoter.

A suitable regulatory element may include an inducible promoter operatively linked to the nucleic acid coding sequence. The invention also provides plant cells transformed with said gene construct and methods including introduction of such a construct into a plant cell and/or induction of expression of a construct within a plant cell, e.g. by application of a suitable stimulus.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Whatever the level of expression is in the absence of the stimulus, expression from any inducible promoter is increased in the presence of the correct stimulus. The preferable situation is where the level of expression increases upon in the presence of the relevant stimulus by an amount effective to alter a phenotypic characteristic i.e. to enhance tolerance of a D-amino acid. Thus an inducible (or "switchable") promoter may be used which causes a basic level of expression in the absence of the stimulus which level is too low to bring about the desired D-amino acid tolerant phenotype (and may in fact be zero). Upon application of the stimulus, expression is increased (or switched on) to a level that causes enhanced D-amino acid tolerance.

Many examples of inducible promoters will be known to those skilled in the art.

Other suitable promoters may include the Cauliflower Mosaic Virus 35S (CaMV 35S) gene promoter that is expressed at a high level in virtually all plant tissues (Benfey et al, (1990) EMBO J 9: 1677-1684); the cauliflower meri 5 promoter that is expressed in the vegetative apical meristem as well as several well localised positions in the plant body, e.g. inner phloem, flower primordia, branching points in root and shoot (Medford, J. I. (1992) *Plant Cell* 4, 1029-1039; Medford et al, (1991) *Plant Cell* 3, 359-370) and the *Arabidopsis thaliana* LEAFY promoter that is expressed very early in flower development (Weigel et al, (1992) *Cell* 69, 843-859). Other examples are disclosed on page 120 of Lindsey and Jones (1989) "Plant Biotechnology in Agriculture" Pub. OU Press, Milton Keynes, UK.

The invention provides a vector comprising a nucleic acid as described above, for example a plasmid or viral expression vector.

As described herein, expression of a polypeptide which has D-amino acid metabolising activity from encoding nucleic acid may be used to select for transformants which contain a nucleic acid construct or vector as described herein.

In some embodiments, a vector may additionally comprise a selectable genetic marker consisting of a chimaeric gene that confers a selectable phenotype such as resistance to an antibiotic such as kanamycin, hygromycin, phosphinotricin, chlorsulfuron, methotrexate, gentamycin, spectinomycin, imidazolinones and glyphosate. This allows for a second level of selection, if desired, in addition to selection using D-amino acid metabolising polypeptide expression.

Another aspect of the present invention provides the use of a nucleic acid as described herein in the production of a transgenic plant. Such a method may allow selection or selective propagation of transgenic plants which comprise foreign genetic material or may be for improving the tolerance of a plant to D-amino acids. Selection is preferably performed by growing the plant or plant cell on a medium which has a defined nitrogen content comprising a D-amino acid i.e. nitrogen in the medium is completely or partially in the form of a D-amino acid.

The identity of the D-amino acid in the medium is determined by the specificity of the heterologous D-amino metabolising polypeptide expressed by the plant or plant cell i.e. the medium contains the D-amino acid substrate of the heterologous D-amino metabolising polypeptide. For example, where heterologous D-serine dehydratase is expressed by a plant, D-serine is present in the growth medium.

Nucleic acids according to the present invention may be provided isolated and/or purified from their natural environment, in substantially pure or homogeneous form, or free or substantially free of other nucleic acids of the species of origin. Where used herein, the term "isolated" encompasses all of these possibilities.

Nucleic acid may of course be double- or single-stranded, cDNA or genomic DNA, or RNA. Expression product may be made by expression from encoding nucleic acid therefore under suitable conditions in suitable host plant cells.

The nucleic acid molecules may be wholly or partially synthetic. In particular, they may be recombinant, in that nucleic acid sequences which are not found together in nature (do not run contiguously) have been ligated or otherwise combined artificially. Alternatively they may have been synthesised directly e.g. using an automated synthesiser.

Those skilled in the art are well able to construct vectors and design protocols for recombinant gene expression, in particular in a plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook & Russell, 2001, Cold Spring Harbor Laboratory Press.

"Vector" is defined to include, inter alia, any plasmid cosmid, phage or *Agrobacterium* binary vector in double or single stranded linear or circular form, which may or may not be self transmissible or mobilizable, and which can transform prokaryotic or eukaryotic host, in particular a plant host, either by integration into the cellular genome or exist extrachromasomally (e.g. autonomous replicating plasmid with an origin of replication).

Specifically included are shuttle vectors by which is meant a DNA vehicle capable, naturally or by design, of replication in two different organisms, which may be selected from actinomyces and related species, bacteria and eukaryotic (e.g. higher plant, mammalia, yeast or fungal) cells.

Many known techniques and protocols for manipulation of nucleic acid, for example in preparation of nucleic acid constructs, mutagenesis, sequencing, introduction of DNA into cells and gene expression, and analysis of proteins, are described in detail in *Protocols in Molecular Biology*, Second Edition, Ausubel et al. eds., John Wiley & Sons, 1992.

Bevan et al (Bevan et al Nucl Acids Res. (1984) 12, 8711-8721) and Guerineau and Mullineaux (Guerineau and Mullineaux (1993) Plant transformation and expression vectors. In: Plant Molecular Biology Labfax (Croy RRD ed) Oxford, BIOS Scientific Publishers, pp 121-148) describe specific procedures and vectors which have previously been used with wide success in plants.

When introducing a nucleic construct into a cell, certain considerations well known to those skilled in the art must be taken into account. There must be available a method of transporting the construct into the cell. Once the construct is within the cell membrane, integration into the endogenous chromosomal material either will or will not occur. The product of expression of the D-amino acid metabolising gene may be directed to a particular intracellular compartment such as the peroxisome or cytosol or expressed ubiquitously. Finally, as far as plants are concerned, the target cell type must be such that cells can be regenerated into whole plants.

Techniques well known to those skilled in the art may be used to introduce nucleic acid constructs and vectors into plant cells to produce transgenic plants of the appropriate D-amino acid tolerant phenotype.

*Agrobacterium* transformation is one method widely used by those skilled in the art to transform plant cells, in particular dicotyledonous species. Production of stable, fertile transgenic plants in almost all economically relevant monocot plants is now routine: (Toriyama, et al. (1988) *Bio/Technology* 6, 1072-1074; Zhang, et al. (1988) *Plant Cell Rep.* 7, 379-384; Zhang, et al. (1988) *Theor Appl Genet* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828). In particular, *Agrobacterium* mediated transformation is now a highly efficient transformation method in monocots (Hiei et al. (1994) *The Plant Journal* 6, 271-282).

Aspects of the invention provide an expression vector for use in such transformation methods which is a disarmed *Agrobacterium* Ti plasmid, and an *Agrobacterium tumefaciens* bacteria comprising such an expression vector.

The generation of fertile transgenic plants has been achieved using this approach in the cereals rice, maize, wheat, oat, and barley (reviewed in Shimamoto, K. (1994) *Current Opinion in Biotechnology* 5, 158-162; Vasil, et al. (1992) *Bio/Technology* 10, 667-674; Vain et al., 1995, *Biotechnology Advances* 13 (4): 653-671; Vasil, 1996, *Nature Biotechnology* 14 page 702). Wan and Lemaux (1994) *Plant Physiol.* 104: 37-48 describe techniques for generation of large numbers of independently transformed fertile barley plants.

Other methods, such as microprojectile or particle bombardment (U.S. Pat. No. 5,100,792, EP-A-444882, EP-A-434616), electroporation (EP 290395, WO 8706614), microinjection (WO 92/09696, WO 94/00583, EP 331083, EP 175966, Green et al. (1987) *Plant Tissue and Cell Culture*, Academic Press) direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d)) may be preferred where *Agrobacterium* transformation is inefficient or ineffective.

In particular, transformation of gymnosperms, such as conifers, may be performed using particle bombardment techniques (Clapham, D. et al. 2000. Scan. J. For. Res. 15: 151.160). Physical methods for the transformation of plant cells are reviewed in Oard, (1991) *Biotech. Adv.* 9: 1-11.

Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency in transforming the target plant species as well as the experience and preference of the user with a particular methodology. It will be apparent to the skilled person that the particular choice of a transformation system to introduce nucleic acid into plant cells is not essential to or a limitation of the invention, nor is the choice of technique for plant regeneration.

Another aspect of the invention provides a method of producing a cell, in particular a plant cell, which includes incorporating an isolated nucleic acid comprising a sequence encoding a D-amino acid metabolising polypeptide operably linked to a plant specific regulatory element, or a vector comprising such a nucleic acid, into the cell by means of transformation. Such a method of producing a cell may include recombining the nucleic acid with the cell genome nucleic acid such that it is stably incorporated therein. A plant may be regenerated from one or more cells transformed as described.

The D-amino acid metabolising polypeptide, the encoding nucleic acid and/or the vector comprising the nucleic acid may be heterogeneous, i.e. exogenous or foreign, to the plant cell transformed therewith.

A method of producing a plant cell may include expressing the nucleic acid and causing or allowing the accumulation of D-amino acid metabolising polypeptide expressed thereby in the cytosol, peroxisome, chloroplast and/or other intracellular compartment of said plant cell.

A method of making such a plant cell may include introducing such a nucleic acid sequence or a suitable vector including the nucleic acid into a plant cell and causing or allowing recombination between the vector and the plant cell genome to introduce the nucleic acid sequence into the genome.

A method may further include sexually or asexually propagating or growing off-spring or a descendant of the plant regenerated from said plant cell.

The invention further encompasses a host cell transformed with a nucleic acid sequence or vector as set forth above, i.e. containing a nucleic acid or vector as described above, especially a plant cell, for example a higher plant cell, or a microbial plant cell. Thus, a host cell, such as a plant cell, including a nucleotide sequence as herein indicated is provided. Within the cell, the nucleotide sequence may be incorporated within the chromosome or may be extra-chromosomal. There may be more than one heterologous nucleotide sequence per haploid genome. This, for example, enables increased expression of the gene product compared with endogenous levels, as discussed below. A nucleic acid coding sequence comprised within a plant cell may be under the control of a plant specific regulatory element which is an externally inducible gene promoter, for example to place expression under the control of the user.

The D-amino acid metabolising polypeptide may be present in the cytosol, peroxisome, or other intracellular compartment of the plant cell. Compartmentalisation of the D-amino acid metabolising polypeptide may be achieved by fusing the nucleic acid sequence encoding the D-amino acid metabolising polypeptide to a sequence encoding a transit peptide to generate a fusion protein. Gene products expressed without such transit peptides generally accumulate in the cytosol.

A nucleic acid that is stably incorporated into the genome of a plant is passed from generation to generation to descendants of the plant, cells of which descendants may express the encoded D-amino acid metabolising polypeptide and so may have enhanced D-amino acid tolerance.

A plant cell may contain a nucleic acid sequence encoding a D-amino acid metabolising polypeptide operably linked to a plant specific regulatory element as a result of the introduction of the nucleic acid sequence into an ancestor cell.

A plant cell as described herein may be comprised in a plant, a plant part or a plant propagule, or an extract or derivative of a plant as described below.

Plants which include a plant cell as described herein are also provided, along with any part or propagule thereof, seed, selfed or hybrid progeny and descendants. Particularly provided are transgenic monocotyledons, dicotelydons, gymnosperms and algae, ferns and mosses. Of particular interest are transgenic higher plants, especially agricultural and forest crops, for example cereals, trees and ornamental flowers, which have been engineered to carry a nucleic acid construct as described above.

Examples of suitable plants include tobacco, cucurbits, carrot, vegetable brassica, melons, capsicums, grape vines, lettuce, strawberry, oilseed brassica, sugar beet, wheat, barley, maize, rice, soyabeans, peas, sorghum, sunflower, tomato, potato, pepper, chrysanthemum, carnation, poplar, eucalyptus, cotton, linseed, hemp, spruce, birch, peanuts, rye and pine.

A plant according to the present invention may be one which does not breed true in one or more properties. Plant varieties may be excluded, particularly registrable plant varieties according to Plant Breeders Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part or propagule of any of these, such as cuttings and seed, which may be used in reproduction or propagation, sexual or asexual. Also encompassed by the invention is a plant which is a sexually or asexually propagated off-spring, clone or descendant of such a plant, or any part or propagule of said plant, off-spring, clone or descendant.

Other aspects of the present invention provide for the use of D-amino acids to selectively grow, regenerate or propagate transgenic plant cells, plant tissue or vascular plants comprising a heterogeneous D-amino acid metabolising polypeptide, as described above.

A method of producing a transgenic plant may comprise;
transforming a plant cell with a nucleic acid or vector comprising a sequence encoding a polypeptide which metabolises a D-amino acid substrate, as described herein; and,
regenerating a plant from the cell on a medium comprising a defined nitrogen source,
wherein the defined nitrogen source comprises or consists of said D-amino acid substrate.

Transformed plant cells are able to utilise the D-amino acid present in the medium as a source of nitrogen. Cells which are untransformed and do not contain the polypeptide with D-amino acid metabolising activity are unable to use this nitrogen source and their growth is hindered as a result. Furthermore, D-amino acid in the medium may have a toxic effect on untransformed plants (which do not possess D-amino acid metabolising activity).

A D-amino acid suitable for use in the medium as a substrate for the D-amino acid metabolising enzyme may be selected from the group consisting of D-arg, D-ser, D-glu, D-ala, D-asp, D-cys, D-gln, D-his, D-ile, D-leu, D-lys, D-met, D-phe, D-pro, D-asn, D-thr, D-trp, D-tyr and D-val.

Preferably, one of D-ser, D-ala, D-glu, D-asn, D-arg, D-lys, D-his or D-asp is used, more preferably D-ala or D-ser. These D-amino acids are toxic to plants which do not contain the appropriate D-amino acid metabolising enzyme.

Other suitable substrates for D-amino acid metabolising enzyme include non-protein amino acids, precursors of amino acids and amino acid derivatives.

Figure 3:
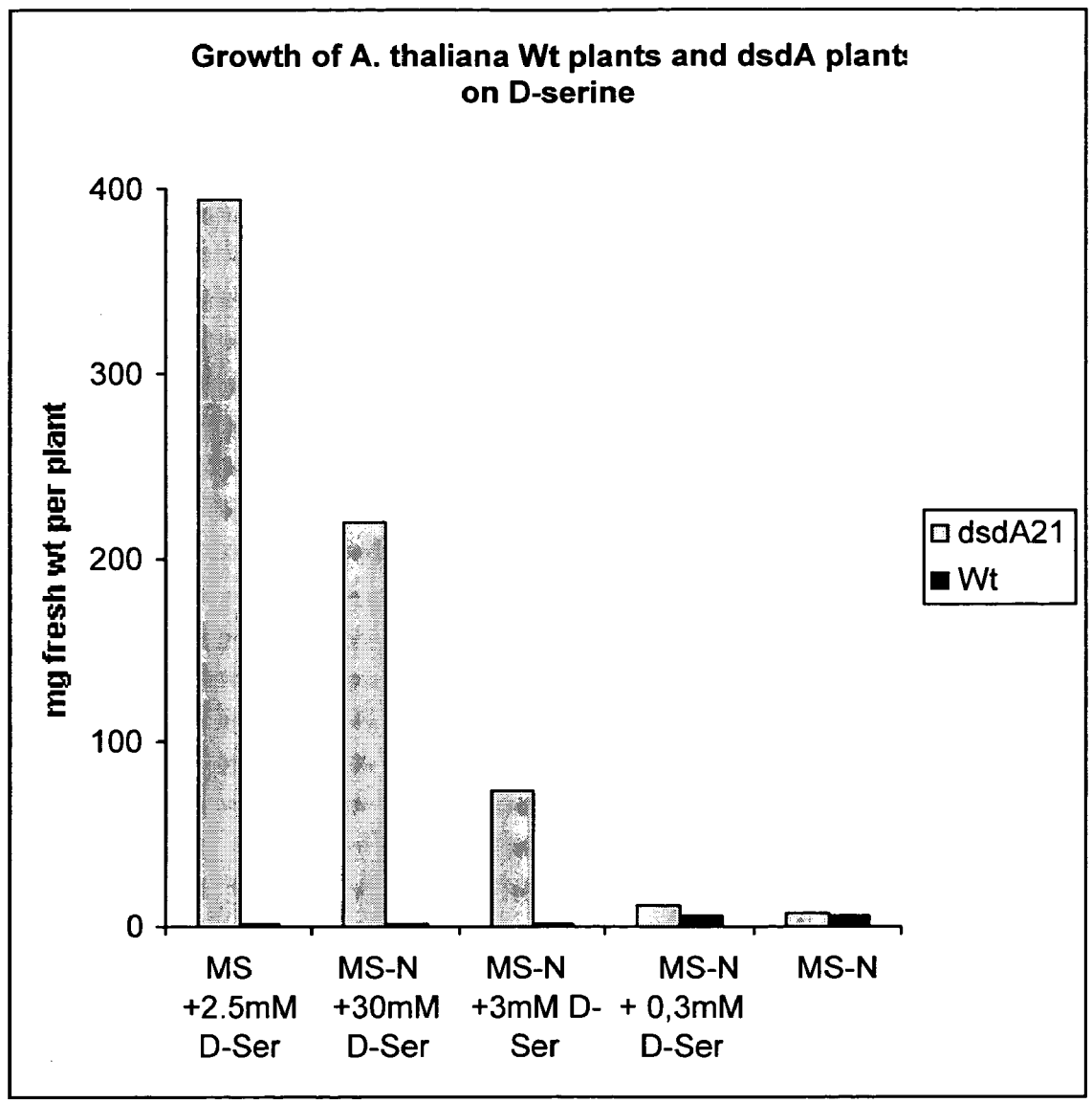
FIG. 3. Fresh weight of wild-type plants and plants transformed with the bacterial gene encoding the enzyme D-serine dehydratase.

Nitrogen is often the element that limits growth of plants in agricultural systems. Compositions in which part or all of the nitrogen content is in the form of one or more D-amino acid (i.e. the nitrogen content of the fertiliser is partially or completely in the form of one or more D-amino acids) are useful as preferential or selective fertilisers for transgenic plants which express an enzyme which metabolises the D-amino acid. Non-transgenic plants, which do not express such an enzyme, will derive reduced benefit from such a fertiliser composition. In some embodiments, the D-amino acid is toxic to such plants and actively hinders or inhibits their growth. For example, D-ser shows toxicity to wild-type plants (FIG. 3).

Another aspect of the present invention provides a composition for selective fertilisation of a transgenic plant comprising a polypeptide which metabolises a D-amino acid substrate as described herein; said composition comprising said D-amino acid substrate.

All or part of the nitrogen content of the composition may be in the form of the D-amino acid substrate (i.e. it may be the only nitrogen source or one of a number of sources of nitrogen in the composition). The proportion of the available nitrogen in the composition which is in the form of D-amino acid may be 0.1%, 1%, 5%, 10%, 20%, 30%, 40%, 50%, 60%, 70%, 80%, 90%, 99% or 100%.

D-amino acid substrates suitable for use in the composition include D-arg, D-ser, D-glu, D-ala, D-asp, D-cys, D-gln, D-his, D-ile, D-leu, D-lys, D-met, D-phe, D-pro, D-asn, D-thr, D-trp, D-tyr or D-val.

Preferably, one of D-ser, D-ala, D-glu, D-arg, D-lys, D-his, D-asn or D-asp is used, more preferably D-ala or D-ser. These D-amino acids are toxic to plants which do not contain a heterogeneous polypeptide which metabolises them, thus providing a 'dual' action in both promoting desired plant growth and inhibiting undesired plant growth.

Other suitable substrates for the D-amino acid metabolising polypeptide include non-protein D-amino acids, precursors of D-amino acids and D-amino acid derivatives.

A method of producing a fertiliser as described above may comprise providing a plant fertiliser composition lacking or substantially lacking a source of nitrogen and admixing with said composition a D-amino acid substrate as described herein.

Another aspect of the present invention provides a selective herbicide composition comprising a D-amino acid as described above.

Such a herbicide will inhibit or reduce the growth of plants which do not contain the appropriate D-amino acid metabolising enzyme, while the growth of transgenic plants which are able to metabolise the D-amino acid will be unaffected or, more preferably, be increased or enhanced.

The composition may comprise 0.1%(w/w) or more, 1%(w/w) or more, 5%(w/w) or more, 10%(w/w) or more, 15%(w/w) or more, 20%(w/w) or more, 25%(w/w) or more or 30%(w/w) or more of the D-amino acid.

Such a herbicide composition may be used in methods of controlling plant growth which comprise treating one or more plants with the composition.

A method of producing such a herbicide composition may include admixing a D-amino acid with a base, carrier or excipient.

Suitable bases, carriers and excipients for use in agricultural, in particular herbicidal, compositions are well-known in the art.

D-amino acids are metabolized by amino acid oxidases to produce hydrogen peroxide ($H_2O_2$). This compound acts as a signal that induces defence reactions in plants. Such reactions are generally triggered by environmental stresses such as excessive light, chilling or pathogen infection.

A plant containing a D-amino acid oxidase enzyme responds to added D-amino acids by increasing $H_2O_2$ and hence by triggering defence reactions. This provides a mechanism by which plant defence responses may be specifically triggered by cultivators. The addition of a D-amino acid to plants expressing the D-amino oxidase gene leads to a burst in endogenous $H_2O_2$ production which induces the normal defensive reaction in these plants. This defensive reaction might be triggered by the cultivator to increase stress tolerance when moving plants from indoor to outdoor conditions, to increase freezing tolerance when there is a risk of frost damage, when known pests and pathogens are building up, or in other situations when an active defence reaction in the plant is of potential advantage.

A method of producing a transgenic plant having an inducible stress response may comprise;

transforming a plant cell with a nucleic acid sequence encoding a D-amino acid oxidase; and, regenerating the transgenic plant from the plant cell.

A method of stimulating the stress tolerance of a transgenic plant may comprise;

expressing in said plant a polypeptide which oxidises a D-amino acid substrate; and, treating said plant with the D-amino acid substrate.

Suitable D-amino acid oxidase polypeptides are described above and exemplified in Table 1 and Table 2.

A suitable dose of D-amino acid stimulates a stress response without causing permanent cellular damage. The precise dosage will vary according to plant type, stage of growth, soil type, temperature and weather conditions but may be readily determined by a skilled person for a particular situation using routine methodology.

In some preferred embodiments, high levels of D-amino acid, for example 0.1 to 50 mM of D-amino acid in the culture medium, more preferably 1 to 10 mM, may be used to induce stress tolerance.

Improved stress tolerance may include enhanced or increased tolerance to environmental stresses such as ultraviolet UV radiation, extreme temperatures, irradiation, and/or pathogen infection, for example bacterial or fungal infection, in particular necrotizing pathogens, relative to normal, untreated plants.

The production of $H_2O_2$ by D-amino acid oxidases as described above or the accumulation of products of D-amino acid metabolism may be deleterious to the transgenic plants, if rates of production are high and/or if production occurs in a cellular compartment which is sensitive to $H_2O_2$ or other metabolic products.

Methods of the present invention can therefore be utilized to selectively remove transgenic plants from mixed populations, or even to remove hybrids between transgenic plants and wild type plants from natural populations.

A method of inhibiting the growth or viability of a transgenic plant which expresses a polypeptide which oxidises a D-amino acid substrate as described herein may comprise; treating said plant with the D-amino acid substrate.

The localisation of expressed D-amino acid oxidase in the peroxisome produces $H_2O_2$ that can be rapidly metabolised by the $H_2O_2$ degrading enzyme catalase. High levels of D-amino acids are therefore required to produce damaging levels of $H_2O_2$. Expression of D-amino acid oxidase in the cytosol, where levels of catalase activity are lower, reduces the amount of D-amino acid required to produce damaging levels $H_2O_2$.

Expression of D-amino acid oxidase in the cytosol may be achieved by removing peroxisome targeting signals or transit peptides from the encoding nucleic acid sequence.

The addition of a D-amino acid may therefore be used to inhibit or reduce the growth or viability of a transgenic plant which has a cytosolic D-amino acid oxidase activity.

A method of inhibiting the growth or viability of a transgenic plant which expresses a polypeptide which oxidises a D-amino acid substrate as described herein may comprise;

causing or allowing accumulation of the polypeptide in the cytosol of said plant, and;

treating said plant with the D-amino acid substrate.

D-amino acids which exhibit low toxicity to wild type plants, for example D-ile, D-asn, or D-gln, but which, following metabolism in transgenic plants containing exogenous D-amino acid oxidases, lead to the production of $H_2O_2$ or other toxic metabolic products, are particularly suitable for use in such methods.

Control experiments may be performed as appropriate in the methods described herein. The performance of suitable controls is well within the competence and ability of a skilled person in the field.

Various further aspects and embodiments of the present invention will be apparent to those skilled in the art in view of the present disclosure. All documents mentioned in this specification are incorporated herein in their entirety by reference.

Certain aspects and embodiments of the invention will now be illustrated by way of example and with reference to the figure described below.

FIG. 1 shows the fresh weight of *Arabidopsis thaliana* plants grown for 20 days in sterile agar culture and supplied with different N sources. Control plants were grown without any nitrogen source.

Figure 2:
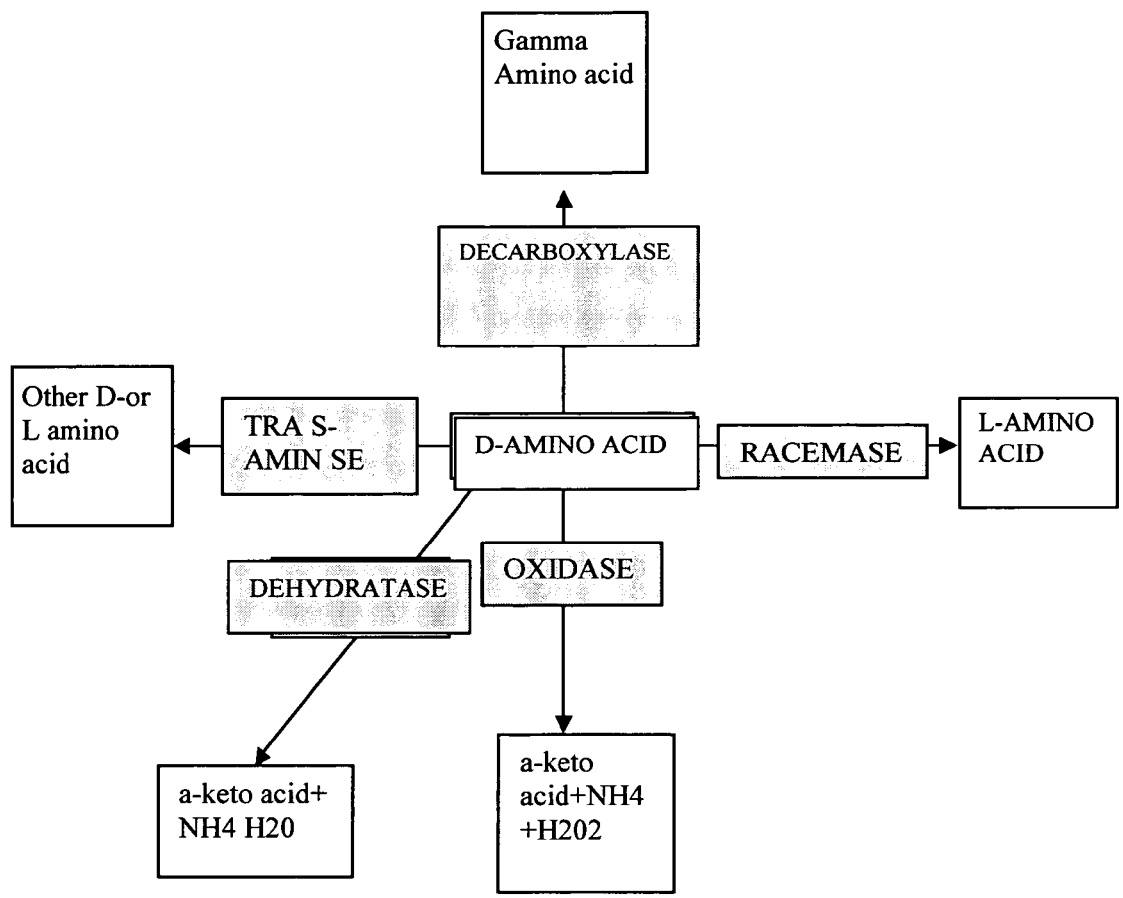
FIG. 2. Examples of potential metabolic conversions of D-amino acids in organisms.

FIG. 2 shows examples of potential metabolic conversions of D-amino acids in organisms FIG. 3 shows the fresh weight of wild type plants (Wt; black bars) and plants transformed with the bacterial gene encoding the enzyme bacterial enzyme D-serine dehydratase (dsdA21, light grey bars) grown on sterile agar and supplied with D-serine at different concentrations (2.5, 30, 3 and 0.3 mM) with (MS) or without (MS-N) the standard nitrogen source, nitrate.

Figure 4:
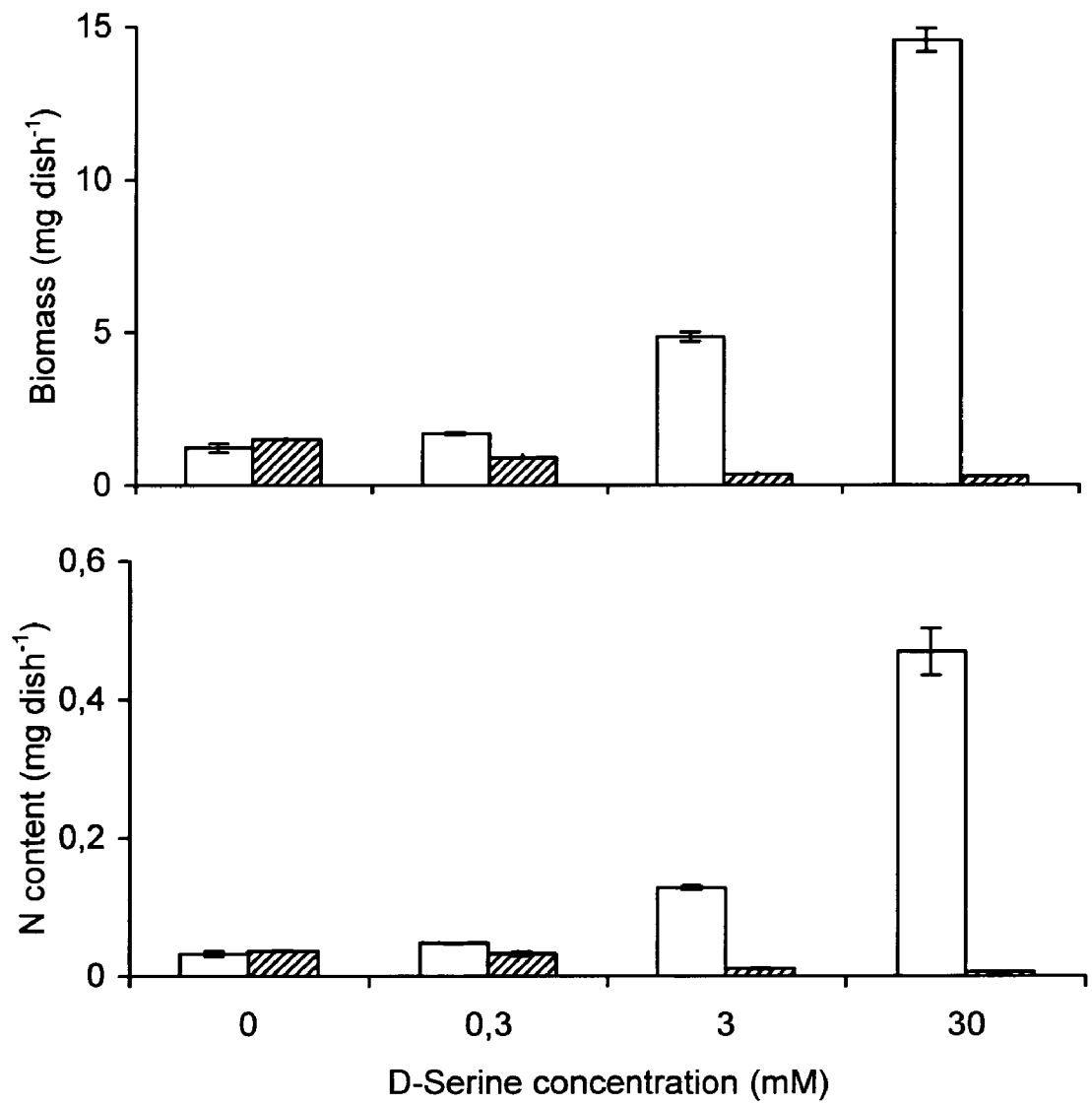
FIG. 4. Biomass (top) and nitrogen content (bottom) at harvest of *Arabidopsis thaliana* grown for 14 days after germination. Open bars are transgenic plants expressing dsdA, hatched bars are wild type plants.

FIG. 4 shows biomass (top) and nitrogen content (bottom) at harvest of *Arabidopsis thaliana* grown for 14 days after germination. Plants were grown on half-strength MS medium without nitrogen sources other than D-serine. Open bars are transgenic plants expressing dsdA, hatched bars are wild type plants. Bars represent mean±standard error, n=4.

Figure 5:
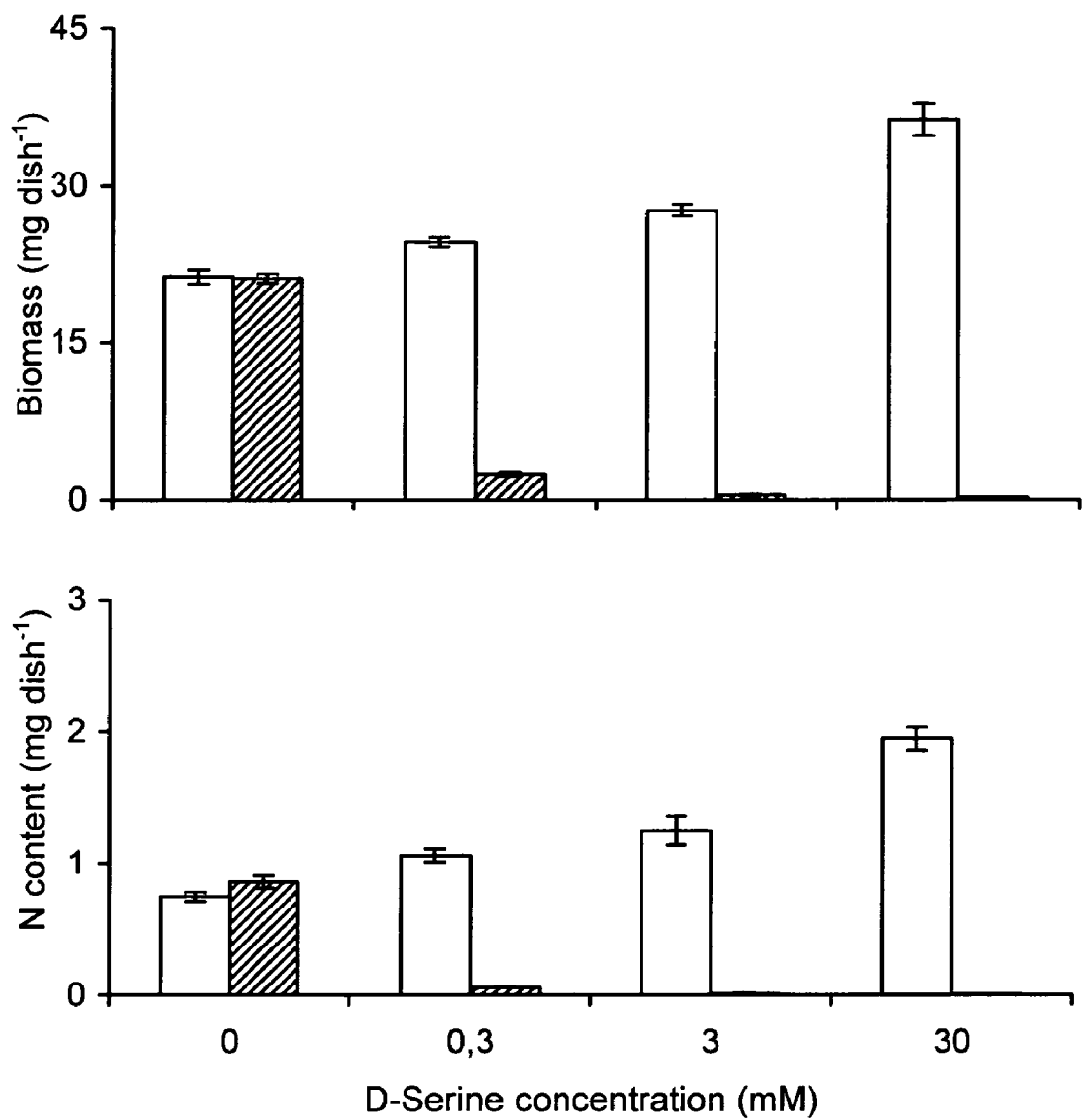
FIG. 5. Biomass (top) and nitrogen content (bottom) at harvest of *Arabidopsis thaliana* grown for 14 days after germination. Open bars are transgenic plants expressing dsdA, hatched bars are wild type plants.

FIG. 5 shows biomass (top) and nitrogen content (bottom) at harvest of *Arabidopsis thaliana* grown for 14 days after germination. Plants were grown on half-strength MS medium with 3 mM nitrate as a basic N supply and amended with different D-serine concentrations. Open bars are transgenic plants expressing dsdA, hatched bars are wild type plants. Bars represent mean±standard error, n=4.

Tables 1 and 2 show examples of polypeptides having D-amino acid metabolising activity which may be used in accordance with the present invention.

Experimental

Methods

*Arabidopsis* Transformation

The *E. coli* gene dsdA (D-serine dehydratase (D-serine deaminase) [EC:4.3.1.18 (SEQ ID NO: 8)] NCBI accession number J01603 (SEQ ID NO: 7)) was amplified by PCR using primers 5'-AATGGATCCTCATCTAAGCGCAAA-GAGACGTACTATGG (SEQ ID NO: 1) and 5'-ATTGGATC-CATGCTGCGTTGAAACGTTATTAACGG (SEQ ID NO: 2). The PCR product was sub-cloned into pT-easy (Promega) and sequenced with DYEnamics cycle sequencing kit, (Amersham Pharmacia biotech). Alignment analysis with the database sequence confirmed successful full length cloning of dsdA. The clone was subsequently ligated into the BamH1 site of the CaMV 35S expression cassette of the binary vector pPCV702Km, which is a disarmed Ti-plasmid of *Agrobacterium tumefaciens*, to generate the vector pPCV702:dsdA. Restriction analysis of this vector with endonuclease confirmed orientation of insertion.

*A. thaliana*, ecotype Col-0, plants were transformed with *Agrobacterium tumefaciens* strain (GV3101:pMP90 RK) through vacuum infiltration (Clough, S. J. & Bent, A. F. Plant Journal. 16, 735-743 (1998)). Transformants were selected on kanamycin containing plates, and molecularly confirmed using northern blots. All analyses were performed using lines homozygous for the transgenic trait.

Transgenic plants expressing D-amino acid oxidase were constructed essentially in the same way as the dsdA plants described above, with the following modifications: The dao1 gene (EC: 1.4.3.3 (SEQ ID NO: 6): NCBIU60066 (SEQ ID NO: 5)) from the yeast *Rhodotorula gracilis* (*Rhodosporidium toruloides*) was cloned with PCR with a cDNA library prepared from yeast grown on D-alanine containing medium to induce expression of the target gene, as a template. PCR primers were 5'-ATTAGATCTTACTACTCGAAGGACGC-CATG (SEQ ID NO: 3) and 5'-ATTAGATCTACAGCCA-CAATTCCCGCCCTA (SEQ ID NO: 4).

PCR was also performed with another set of primers, with one primer flanking the 5' end of the open reading frame as set out above and a 3' primer excluding the last 6 nucleotides. The last nine nucleotides encode the signal peptide SKL, which guides the protein to the peroxisome sub-cellular organelle.

The resulting amplified sequences encode proteins which have the same amino acid sequence but which differ in the respect of their location in the cell. The truncated polypeptide, without the signal peptide, is expressed in the cytosol, while the full-length polypeptide is expressed in the peroxisome.

Plant Culture

*A. thaliana* seeds from non-transformed plants and D-Serine ammonia-lyase transformed plants were surface sterilised with 70% ethanol and 0.1% Tween 80 for 10 minutes and rinsed briefly in 95% ethanol. 10 seeds were sown in each plate and the plates where thereafter sealed with gas permeable tape. The growth medium was half-strength MS (Murashige, T. & Skoog, F. Physiol Plant 15, 310-313 (1962)) (with 0.5% w/v sucrose and 0.8% w/v agar) with nitrogen either excluded or included as 3 mM nitrate. Filter sterilised D-serine was added to the medium after autoclaving. Plants were grown for 14 days after germination with a 16 h photoperiod at 24° C. Plants were extracted from the plates, washed three times in 0.5 mM $CaCl_2$ and thereafter dried at 40° C. for 48 hours before dry weight measurements. The N content was determined on dried plants using an elemental analyser (PerkinElmer 2400 CHN). Biomass and nitrogen content were measured on a per plate basis and there were 10 plants per plate. Six independent transgenic lines were evaluated for their capacity to grow on D-serine and no substantial difference was noticed among the lines, although dsdA transcript levels varied substantially according to northern blot analyses.

For spruce transformation, the expression vector had a pUC8 back bone with a 35S expression cassette with dsdA and a pUbi-Bar (Ubiquitin promoter with the Bar gene that confers basta resistance) cassette for the purpose of basta selection. The transformation method used was particle bombardment of a cell suspension.

Results

Effect of D-Amino Acids of Wild Type Plant Growth

The growth of wild-type *Arabidopsis thaliana* plants in sterile agar culture using different N sources was observed. The results are shown in FIG. 1. Little or no growth was observed for plants grown on D-amino acid media.

Seeds from *Solanum esculentum, Hordeum vulgare, Zea mays, Populus tremuloides, Nicotiana tabacum* and *Arabidopsis thaliana* were surface sterilised and grown for two to three weeks on agar media identical to the nitrate free media described above and amended with 0, 0.3, 3 and 30 mM D-serine. Growth of *Lycopersicon esculentum, Populus tremuloides, Nicotiana tabacum* and *Arabidopsis thaliana* was observed to be inhibited at a concentration of 3 mM D-serine in the media, while growth of *Zea mays* and *Hordeum vulgare* was inhibited at 30 mM.

D-serine and several other D-amino acids were observed to inhibit growth of wild-type *A. thaliana* and other species. For *A. thaliana*, clear growth inhibition is observed at a concentration of 0.3 mM D-serine in the growth medium and total growth inhibition occurs at 3 mM (FIG. 3).

Somatic embryonic cell suspension cultures of *Picea abies* were grown on a range of D-serine concentrations; 0, 0.3, 3 and 30 mM D-serine. D-serine was lethal to cells at and above 3 mM. It was found to be possible to select dsdA-transformed embryos on a D-serine medium containing 3 mM of D-serine.

These results demonstrate the herbicidal properties of D-amino acids on wild-type plants.

*Arabidopsis thaliana* Expressing *E. coli* D-Serine Ammonia-Lyase

*Arabidopsis thaliana* was transformed with the *E. coli* gene dsdA, encoding D-serine ammonia-lyase [EC:4.3.1.18] under the control of the CaMV 35S promoter. D-serine ammonia-lyase converts D-serine into the products ammonium, pyruvate and water, which are readily utilized by plants and transformed plants can grow on D-serine as their only N source.

Transgenic *Arabidopsis thaliana* plants expressing the gene encoding D-serine dehydratase were grown sterile alongside wild type plants on agar for 20 days on standard MS medium supplemented with varying concentrations of D-serine as the sole N source (30 mM, 3 mM, 0.3 mM) along with a control lacking any nitrogen.

Minimal growth of both transgenic and wild type plants was observed on the control medium lacking nitrogen. Both growth and N content of the transgenic plants was observed to increase significantly (analysis of variance, $p<0.0001$) with increasing D-serine concentration (FIG. 4 top and bottom). No increase in the growth of the wild-type plants was observed (FIG. 3). In the presence of a basic level of nitrate, growth and nitrogen content of transgenic plants also increased significantly ($p<0.0001$) with increasing D-serine concentration, while the opposite response is found for wild-type plants (FIG. 5). This indicates that D-serine has a toxic effect on the wild type plant but not on the transgenic plant. Within the observed range of D-Ser, the transgenic plants showed no toxicity symptoms.

The relative growth response to increased D-serine concentration is similar whether or not the transgenic plants receive a basic supply of nitrate (FIG. 4(top) and 5(top)). The corresponding response in plant N content is, however, higher in plants supplied with both D-serine and nitrate (FIG. 4(bottom) and 5(bottom)). At equal concentration, growth of plants on nitrate is significantly higher than on D-serine (FIG. 4(top) and 5(top)). The N concentration of plants grown on 3 mM D-serine is, however, significantly lower than plants grown on 3 mM nitrate (ANOVA, $p<0.0001$). The cause of the lower growth on D-serine is unknown but the relatively low N concentration of D-serine grown plants may indicate a lower uptake rate of this N form compared to that of nitrate.

Successful selection of transgenic *Arabidopsis* plants was also achieved by spraying 30 mM D-Serine three times during one week onto *Arabidopsis* seedlings grown on soil.

*Arabidopsis thaliana* Expressing *E. coli* D-glutamate Racemase

Construction of *Arabidopsis thaliana* plants expressing *E. coli* D-glutamate racemase was made essentially in the same way as described above. The gene murI, NCBI accession number AAC76949, encodes the racemase EC: 5.1.1.3. The primers for cloning of the gene were designed to flank the open reading frame on the basis of the database sequence.

The transgenic plants were observed to survive and grow on conventional media and conventional nitrogen sources.

*Arabidopsis thaliana* which Metabolise D-Amino Acids with a Simultaneous Production of Hydrogen Peroxide Construction of *Arabidopsis thaliana* plants expressing two variants of *Rhodotorula gracilis* D-amino acid oxidase were made as described above.

These transgenic plants were observed to survive and grow on conventional media with a conventional source of nitrogen.

Similar results to those described for plants expressing D-serine ammonia-lyase were obtained when expressing the yeast (*Rhodotorula gracilis*) gene encoding D-amino acid oxidase (EC 1.4.3.3) in *A. thaliana* i.e. growth and N content of transgenic plants was increased relative to the wild-type plants on media containing D-amino acids.

D-amino acid oxidase has a range of substrate D-amino acids and tests with D-alanine and D-serine confirmed that the D-amino acid oxidase enzyme could also convert these N forms into accessible N sources and thus alleviate the toxicity caused by D-alanine and D-serine.

30 mM D-Asn was observed to effectively stop plants expressing D-amino oxidase from growing in sterile agar culture. No germination was observed for D-amino oxidase expressing plants, indicating a total inhibition of growth. Wt plants were observed to germinate and grow slowly to produce small green shoots. Thus, wild type growth was only partially retarded and wild type plants were rescued and placed in soil to recover.

D-ile was found to be even more effective in hindering growth of transgenic plants expressing dao1 with no visible inhibitory effect on wild type plants. Wild type *Arabidopsis* was found to increase in growth with increasing D-ile concentration, within the examined interval (0.3 to 30 mM).

Although no significant differences were observed between cytosolic and peroxisomal expressed D-amino oxidase, the peroxisomal construction was found to be marginally more effective than the cytosolic version in respect of inhibiting the germination of the D-amino oxidase plant on 30 mM D-Asn. However, both constructs are inhibited significantly more than the wild-type and may thus be used for conditional negative selection.

Poplar and Tobacco expressing *E. coli* Gene dsdA (D-Serine Dehydratase)

Poplar and tobacco were transformed using the same vector and transformation protocol described above for the transformation of *Arabidopsis*.

3 mM and 30 mM D-Ser was observed to be sufficient to stop all shoot formation of wild type poplar and tobacco respectively, when placed on shoot inducing media. However, tobacco and poplar transformed with dsdA were found to be resistant to D-Ser at concentrations exceeding 30 mM.

Transgenic plants produced as described herein metabolise N forms that are inaccessible to other plants. This allows added N to be targeted to such plants in mixed plant settings. Applied D-amino acids have a dual effect in promoting growth of transgenic plants and inhibiting growth of other plants and this may create synergistic effects when used in agriculture. Direct control over N resources may reduce the amount of N that is needed for good growth, potentially reducing the environmental pressure caused by unnecessarily high N loads. Furthermore, in cultivation systems in which crop plants have a competitive advantage by accessing a specific resource of N, the demand for weed control may decrease, reducing the overall need of herbicides.

TABLE 1

| Enzyme | Accession number (Brenda protein database) | Source organism | Substrate |
|---|---|---|---|
| Dehydratase | | | |
| D-Serine ammonia lyase (also known as D-serine dehydratase) | EC-number 4.3.1.18 | E. intermedia E. coli Klebsiella pneumoniae Chicken | D-Ser D-Thr D-allothreonine |
| Oxidases | | | |
| D-Amino acid oxidase | EC-number 1.4.3.3 | Pig Human Rat Candida tropicalis Trigonopsis variabilis Neuspora crassa Chlorella vulgaris Rhodotorula gracilis | Most D-amino acid |
| D-Glutamate oxidase | EC-number 1.4.3.7 | Octopus vulgaris Orconectes limosus | D-Asp D-Glu |
| D-Aspartate oxidase | EC-number 1.4.3.1 | Rabbit Human Pig Bovine Bos taurus | D-Asp D-Glu N-methyl-D-Asp Meso-2,3-diaminosuccenate (relevancy not known) cis-Thiazolidine-2,4-dicarboxylate (relevancy not known) |
| Racemases | | | |
| D-Glutamate racemase | EC-number 5.1.1.3 | Lactobacillus sp Pediococcus pentosaceus E. coli | D/L-Glu |
| Transaminases | | | |
| D-Methionine transaminase | EC-number 2.6.1.21 | Brassica sp mitochondria | D-Methionine |
| D-Alanine transaminase | EC-number 2.6.1.21 | Bacillus sp. Listeria monocytogenes Thermophilic bacterium | D-Arg D-Ala D-Asp D-Glu D-Leu D-Lys D-Met D-Phe D-Norvaline |

TABLE 2

D-AMINO ACID TRANSFERASE/D-AMINO ATRANSAMINASE

| P54692 | D-ALANINE AMINOTRANSFERASE (EC 2.6.1.21) (DAAT). Bacillus licheniformis. DAT. |
| P54693 | D-ALANINE AMINOTRANSFERASE (EC 2.6.1.21) (DAAT). Bacillus sphaericus. DAT. |
| P19938 | D-ALANINE AMINOTRANSFERASE (EC 2.6.1.21) (DAAT). Bacillus sp. (strain YM-1). DAT. |
| O07597 | D-ALANINE AMINOTRANSFERASE (EC 2.6.1.21) (DAAT). Bacillus subtilis. DAT. |
| O85046 | D-ALANINE AMINOTRANSFERASE (EC 2.6.1.21) (DAAT). Listeria monocytogenes. DAT. |
| P54694 | D-ALANINE AMINOTRANSFERASE (EC 2.6.1.21) (DAAT). Staphylococcus haemolyticus. DAT. |

TABLE 2-continued

D-ASPARTATE OXIDASE

| P31228 | D-ASPARTATE OXIDASE (EC 1.4.3.1) (DASOX) (DDO). Bos taurus (Bovine). DDO. |
| Q99489 | D-ASPARTATE OXIDASE (EC 1.4.3.1) (DASOX) (DDO). Homo sapiens (Human). DDO. |
| Q9UJ09 | DJ261K5.2 (D-ASPARTATE OXIDASE (EC 1.4.3.1)). Homo sapiens (Human). DDO. |
| Q9TRA3 | D-ASPARTATE OXIDASE (EC 1.4.3.1) (FRAGMENT). Bos taurus (Bovine). |

D-SERINE DEHYDRATASE

| P54555 | PROBABLE D-SERINE DEHYDRATASE (EC 4.2.1.14) (D-SERINE DEAMINASE). Bacillus subtilis. YQJR. |
| P00926 | D-SERINE DEHYDRATASE (EC 4.2.1.14) (D-SERINE DEAMINASE). Escherichia coli. DSDA. |
| Q9KL72 | D-SERINE DEHYDRATASE. Vibrio cholerae. VCA0875. |
| Q9KC12 | D-SERINE DEHYDRATASE (EC 4.2.1.14). Bacillus halodurans. DSDA. |

D-AMINO ACID OXIDASE

| Q19564 | PUTATIVE D-AMINO ACID OXIDASE (EC 1.4.3.3) (DAMOX) (DAO) (DAAO). Caenorhabditis elegans. F18E3.7. |
| P24552 | D-AMINO ACID OXIDASE (EC 1.4.3.3) (DAMOX) (DAO) (DAAO). Fusarium solani (subsp. pisi) (Nectria haematococca). |
| P14920 | D-AMINO ACID OXIDASE (EC 1.4.3.3) (DAMOX) (DAO) (DAAO). Homo sapiens (Human). DAO OR DAMOX. |
| P18894 | D-AMINO ACID OXIDASE (EC 1.4.3.3) (DAMOX) (DAO) (DAAO). Mus Musculus (Mouse). DAO or DAO1. |
| P00371 | D-AMINO ACID OXIDASE (EC 1.4.3.3) (DAMOX) (DAO) (DAAO). Sus scrofa (Pig). DAO. |
| P22942 | D-AMINO ACID OXIDASE (EC 1.4.3.3) (DAMOX) (DAO) (DAAO). Oryctolagus cuniculus (Rabbit). DAO. |
| O35078 | D-AMINO ACID OXIDASE (EC 1.4.3.3) (DAMOX) (DAO) (DAAO). Rattus norvegicus (Rat). DAO. |
| P80324 | D-AMINO ACID OXIDASE (EC 1.4.3.3) (DAMOX) (DAO) (DAAO). Rhodosporidium toruloides (Yeast) (Rhodotorula gracilis). DAO. |
| Q99042 | D-AMINO ACID OXIDASE (EC 1.4.3.3) (DAMOX) (DAO) (DAAO). Trigonopsis variabilis. DAO1. |
| Q9Y7N4 | PUTATIVE D-AMINO ACID OXIDASE (EC 1.4.3.3) (DAMOX) (DAO) (DAAO). Schizosaccharomyces pombe (Fission yeast). SPCC1450.001739 |
| O01739 | SIMILAR TO D-AMINO ACID OXIDASE. Caenorhabditis elegans. F20H11.5. |
| Q28382 | D-AMINO ACID OXIDASE (FRAGMENT). Sus scrofa (Pig). DAO. |
| O33145 | PUTATIVE D-AMINO ACID OXIDASE (EC 1.4.3.3). Mycobacterium leprae. AAO. |
| Q9X7P6 | PUTATIVE D-AMINO ACID OXIDASE. Streptomyces coelicolor. SC5F2A. 23C. |
| Q9JXF8 | D-AMINO ACID OXIDASE FLAVOPROTEIN, PUTATIVE. Neisseria meningitidis (serogroup B). NMB2068. |
| Q9Z302 | D-AMINO ACID OXIDASE. Cricetulus griseus (Chinese hamster). |
| Q9Z1M5 | D-AMINO ACID OXIDASE. Cavia porcellus (Guinea pig). |

RACEMASE

| O68006 | GLUTAMATE RACEMASE (EC 5.1.1.3)]. Bacillus licheniformis. BACA. |
| Q9L870 | GLUTAMATE RACEMASE (EC 5.1.1.3). Anabaena sp. (strain PCC 7120). MURI. |
| O66662 | GLUTAMATE RACEMASE (EC 5.1.1.3). Aquifex aeolicus. MURI OR AQ_325. |
| P56868 | GLUTAMATE RACEMASE (EC 5.1.1.3). Aquifex pyrophilus. MURI. |
| O31332 | GLUTAMATE RACEMASE (EC 5.1.1.3). Bacillus cereus. MURI OR GLR. |
| O82826 | GLUTAMATE RACEMASE (EC 5.1.1.3). Bacillus subtilis var. natto. MURI OR GLR. |
| P52972 | GLUTAMATE RACEMASE (EC 5.1.1.3). Bacillus sphaericus. MURI OR GLR. |

TABLE 2-continued

| | |
|---|---|
| P94556 | GLUTAMATE RACEMASE (EC 5.1.1.3). *Bacillus subtilis*. RACE. |
| O51127 | GLUTAMATE RACEMASE (EC 5.1.1.3). *Borrelia burgdorferi* (Lyme disease spirochete). MURI OR BB0100. |
| Q9XDZ7 | GLUTAMATE RACEMASE (EC 5.1.1.3). *Brevibacterium lactofermentum*. MURI. |
| P57619 | GLUTAMATE RACEMASE (EC 5.1.1.3). *Buchnera aphidicola* (subsp. *Acyrthosiphon pisum*) (AcyrthosipMURI OR BU554. |
| Q9PM24 | GLUTAMATE RACEMASE (EC 5.1.1.3). *Campylobacter jejuni*. MURI OR CJ1652. |
| Q9L4V5 | GLUTAMATE RACEMASE (EC 5.1.1.3). *Carnobacterium* sp. (strain St2). MURI OR GLR. |
| Q9RU10 | GLUTAMATE RACEMASE (EC 5.1.1.3). *Deinococcus radiodurans*. MURI OR DR1586. |
| P22634 | GLUTAMATE RACEMASE (EC 5.1.1.3). *Escherichia coli*. MURI OR DGA OR GLR. |
| P52973 | GLUTAMATE RACEMASE (EC 5.1.1.3). *Haemophilus influenzae*. MURI OR HI1739.2. |
| Q9ZLT0 | GLUTAMATE RACEMASE (EC 5.1.1.3). *Helicobacter pylori* J99 (*Campylobacter pylori* J99). MURI OR GLR OR HP0549. |
| P56068 | GLUTAMATE RACEMASE (EC 5.1.1.3). *Helicobacter pylori* (*Campylobacter pylori*). MURI OR GLR OR HP0549. |

TABLE 2-continued

| | |
|---|---|
| P48797 | GLUTAMATE RACEMASE (EC 5.1.1.3). *Lactobacillus brevis*. MURI. |
| Q03469 | GLUTAMATE RACEMASE (EC 5.1.1.3). *Lactobacillus fermentum*. MURI. |
| P46705 | GLUTAMATE RACEMASE (EC 5.1.1.3). *Mycobacterium leprae*. MURI OR B1549_C2_210. |
| Q10626 | GLUTAMATE RACEMASE (EC 5.1.1.3). *Mycobacterium tuberculosis*. MURI OR RV1338 OR MTCY130.23 OR MTCY02B10.02. |
| Q9RQW7 | GLUTAMATE RACEMASE (EC 5.1.1.3). *Neisseria meningitidis* (serogroup A), andMURI OR GLR OR NMA2026 OR NMB0458. |
| Q08783 | GLUTAMATE RACEMASE (EC 5.1.1.3). *Pediococcus pentosaceus*. MURI. |
| P40723 | GLUTAMATE RACEMASE (EC 5.1.1.3) (FRAGMENT). *Salmonella typhimurium*. MURI. |
| P52974 | GLUTAMATE RACEMASE (EC 5.1.1.3). *Staphylococcus haemolyticus*. MURI OR DGA. |
| P73737 | GLUTAMATE RACEMASE (EC 5.1.1.3). *Synechocystis* sp. (strain PCC 6803). MURI OR SLR1746. |
| O83421 | GLUTAMATE RACEMASE (EC 5.1.1.3). *Treponema pallidum*. MURI OR TP0406. |
| Q9KVI7 | GLUTAMATE RACEMASE (EC 5.1.1.3). *Vibrio cholerae*. MURI OR VC0158. |

The invention claimed is:

1. A system for selective fertilization of a plant, comprising
   (a) a plant comprising a plant cell comprising an expression vector, the vector comprising an isolated nucleic acid comprising a nucleotide sequence encoding a polypeptide which has D-amino acid metabolizing activity, wherein the nucleotide sequence is operably linked to a heterologous plant specific regulatory element that directs expression of the nucleic acid within the plant cell; and
   (b) a fertilizer composition comprising a D-amino acid and an agricultural base, carrier, or excipient.

2. The system of claim herein the D-amino acid is suitable as a substrate for the polypeptide which has D-amino acid metabolizing activity of part (a).

3. The system of claim 1, further comprising a plant which does not comprise a nucleotide sequence encoding a polypeptide which has D-amino acid metabolizing activity.

4. A method of controlling plant growth comprising providing the system of claim 1, and treating the plant with the fertilizer composition.

5. A method for selective plant growth comprising providing the system of claim 1, providing a plant which does not comprise a nucleotide sequence encoding a polypeptide which has D-amino acid metabolizing activity, and treating the plants with the fertilizer composition.

6. A method of producing the system of claim 1, comprising
a) producing a transgenic plant from a transformed plant cell, which plant cell comprises an expression vector comprising an isolated nucleic acid comprising a nucleotide sequence encoding a polypeptide which has a D-amino acid metabolizing activity, wherein the nucleotide sequence is operably linked to a heterologous plant specific regulatory element, which directs expression of the nucleic acid within a plant cell; and
b) providing a fertilizer composition comprising a D-amino acid and an agricultural base, carrier, or excipient.

7. The method of claim 6, wherein the D-amino acid is suitable as a substrate for the polypeptide which has D-amino acid metabolizing activity of part (a).

* * * * *

UNITED STATES PATENT AND TRADEMARK OFFICE
CERTIFICATE OF CORRECTION

PATENT NO. : 7,741,540 B2
APPLICATION NO. : 11/473552
DATED : June 22, 2010
INVENTOR(S) : Torgny Näsholm et al.

Page 1 of 1

It is certified that error appears in the above-identified patent and that said Letters Patent is hereby corrected as shown below:

In Claim 2, in column 28, on line 54, "2. The system of claim herein the D-amino acid is suitable" should read -- 2. The system of claim 1, wherein the D-amino acid is suitable --;

Signed and Sealed this
Eighth Day of March, 2011

David J. Kappos
*Director of the United States Patent and Trademark Office*

```
                          SEQUENCE LISTING

<160> NUMBER OF SEQ ID NOS: 8

<210> SEQ ID NO 1
<211> LENGTH: 38
<212> TYPE: DNA
<213> ORGANISM: Artificial sequence
<220> FEATURE:
<223> OTHER INFORMATION: Description of artificial sequence: primer

<400> SEQUENCE: 1
aatggatcct catctaagcg caaagagacg tactatgg                           38

<210> SEQ ID NO 2
<211> LENGTH: 35
<212> TYPE: DNA
<213> ORGANISM: Artificial sequence
<220> FEATURE:
<223> OTHER INFORMATION: Description of artificial sequence: primer

<400> SEQUENCE: 2
attggatcca tgctgcgttg aaacgttatt aacgg                              35

<210> SEQ ID NO 3
<211> LENGTH: 30
<212> TYPE: DNA
<213> ORGANISM: Artificial sequence
<220> FEATURE:
<223> OTHER INFORMATION: Description of artificial sequence: primer

<400> SEQUENCE: 3
attagatctt actactcgaa ggacgccatg                                    30

<210> SEQ ID NO 4
<211> LENGTH: 30
<212> TYPE: DNA
<213> ORGANISM: Artificial sequence
<220> FEATURE:
<223> OTHER INFORMATION: Description of artificial sequence: primer
```

<400> SEQUENCE: 4

```
attagatcta cagccacaat tcccgccta                                    30
```

<210> SEQ ID NO 5
<211> LENGTH: 1160
<212> TYPE: DNA
<213> ORGANISM: Rhodosporidium toruloides

<400> SEQUENCE: 5

```
atgcactcgc agaagcgcgt cgttgtcctc ggatcaggcg ttatcggtct gagcagcgcc    60
ctcatcctcg ctcggaaggg ctacagcgtg catattctcg cgcgcgactt gccggaggac   120
gtctcgagcc agactttcgc ttcaccatgg gctggcgcga attggacgcc tttcatgacg   180
cttacagacg gtcctcgaca agcaaaatgg gaagaatcga ctttcaagaa gtgggtcgag   240
ttggtcccga cgggccatgc catgtggctc aaggggacga ggcggttcgc gcagaacgaa   300
gacggcttgc tcgggcactg gtacaaggac atcacgccaa attaccgccc cctcccatct   360
tccgaatgtc cacctggcgc tatcggcgta acctacgaca ccctctccgt ccacgcacca   420
aagtactgcc agtaccttgc aagagagctg cagaagctcg gcgcgacgtt tgagagacgg   480
accgttacgt cgcttgagca ggcgttcgac ggtgcggatt tggtggtcaa cgctacggga   540
cttggcgcca agtcgattgc gggcatcgac gaccaagccg ccgagccaat ccgcgggcaa   600
accgtcctcg tcaagtcccc atgcaagcga tgcacgatgg actcgtccga ccccgcttct   660
cccgcctaca tcattccccg accaggtggc gaagtcatct gcggcgggac gtacggcgtg   720
ggagactggg acttgtctgt caacccagag acggtccagc ggatcctcaa gcactgcttg   780
cgcctcgacc cgaccatctc gagcgacgga acgatcgaag catcgaggt cctccgccac   840
aacgtcggct gcgacctgc acgacgaggc ggaccccgcg ttgaggcaga acggatcgtc   900
ctgcctctcg accggacaaa gtcgcccctc tcgctcggca ggggcagcgc acgagcggcg   960
aaggagaagg aggtcacgct tgtgcatgcg tatggcttct cgagtgcggg ataccagcag  1020
agttggggcg cggcggagga tgtcgcgcag ctcgtcgacg aggcgttcca gcggtaccac  1080
ggcgcggcgc gggagtcgaa gttgtagggc gggatttgtg gctgtattgc gggcatctac  1140
aagaaaaaaa aaaaaaaaa                                              1160
```

<210> SEQ ID NO 6
<211> LENGTH: 368
<212> TYPE: PRT
<213> ORGANISM: Rhodosporidium toruloides

<400> SEQUENCE: 6

```
Met His Ser Gln Lys Arg Val Val Val Leu Gly Ser Gly Val Ile Gly
  1               5                  10                  15

Leu Ser Ser Ala Leu Ile Leu Ala Arg Lys Gly Tyr Ser Val His Ile
             20                  25                  30

Leu Ala Arg Asp Leu Pro Glu Asp Val Ser Ser Gln Thr Phe Ala Ser
         35                  40                  45

Pro Trp Ala Gly Ala Asn Trp Thr Pro Phe Met Thr Leu Thr Asp Gly
     50                  55                  60

Pro Arg Gln Ala Lys Trp Glu Glu Ser Thr Phe Lys Lys Trp Val Glu
 65                  70                  75                  80

Leu Val Pro Thr Gly His Ala Met Trp Leu Lys Gly Thr Arg Arg Phe
                 85                  90                  95
```

| | | | | | | | | | | | | |
|---|---|---|---|---|---|---|---|---|---|---|---|---|
|Ala|Gln|Asn|Glu|Asp|Gly|Leu|Leu|Gly|His|Trp|Tyr|Lys|Asp|Ile|Thr|
| | |100| | | |105| | | |110| | |

Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Met Asp Ser Ser Asp Pro Ala Ser Pro Ala Tyr Ile
        210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
        290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 7
<211> LENGTH: 1989
<212> TYPE: DNA
<213> ORGANISM: Escherichia coli

<400> SEQUENCE: 7

```
accctatcac tgccatgttt atcgccgtgt ttgtcgccta ttatgtgttg ggtatacggt      60
ccagcatatg agcatgggga cgatgctcac acatacggaa aatggcttcg gttctattgc     120
taatattttg ctgattatcg gggccggagg cgcattcaac gcattttaaa agcagcagt     180
ctcgctgata cgctggcagt tattctctcc aatatgcata tgcacccgat tcttctggcc    240
tggttagtgg ctcttattct gcatgcggca gtgggctccg ctaccgtggc aatgatgggg    300
gcaacggcaa ttgttgcacc catgctgccg ctgtatcccg acatcagccc ggaaattatt    360
gcgattgcta tcggttcagg tgcaattggc tgcactatcg ttacggactc gcttttctgg    420
ctagtgaagc aatattgcgg cgctacgctc aatgaaacat ttaaatacta tacgacagcg    480
acatttatcg cttcagtcgt cgctctggcg ggcacattcc tgctgtcatt tatcatctaa    540
gcgcaaagag acgtactatg gaaaacgcta aaatgaactc gctcatcgcc cagtatccgt    600
```

```
tggtaaagga tctggttgct cttaaagaaa ccacctggtt taatcctggc acgacctcat    660
tggctgaagg tttaccttat gttggcctga ccgaacagga tgttcaggac gcccatgcgc    720
gcttatcccg ttttgcaccc tatctggcaa aagcatttcc tgaaactgct gccactgggg    780
ggattattga atcagaactg gttgccattc gagctatgca aaaacggctg aaaaagaat     840 atcagcaacc gatcagcggg caactgttac tgaaaaaaga tagccatttg cccatttccg    900
gctccataaa agcacgcggc gggatttatg aagtcctggc acacgcagaa aaactggctc    960
tggaagcggg gttgctgacg cttgatgatg actacagcaa actgctttct ccggagttta    1020
aacagttctt tagccaatac agcattgctg tgggctcaac cggaaatctg ggttatcaa     1080 tcggcattat gagcgcccgc attggcttta aggtgacagt tcatatgtct gctgatgccc    1140
gggcatggaa aaaagcgaaa ctgcgcacgc atggcgttac ggtcgtggaa tatgagcaag    1200
attatggtgt tgccgtcgag gaaggacgta aagcagcgca gtctgacccg aactgtttct    1260
ttattgatga cgaaaattcc cgcacgttgt tccttgggta ttccgtcgct ggccagcgtc    1320
ttaaagcgca atttgcccag caaggccgta tcgtcgatgc tgataaccct ctgtttgtct    1380
atctgccgtg tggtgttggc ggtggtcctg gtggcgtcgc attcgggctt aaactggcgt    1440
ttggcgatca tgttcactgc ttttttgccg aaccaacgca ctcccttgt atgttgttag     1500 gcgtccatac aggattacac gatcagattt ctgttcagga tattggtatc gacaaccta     1560 ccgcagcgga tggccttgca gttggtcgcg catcaggctt tgtcgggcgg gcaatggagc    1620
gtctgctgga tggcttctat acccttagcg atcaaaccat gtatgacatg cttggctggc    1680
tggcgcagga agaaggtatt cgtcttgaac cttcggcact ggcgggtatg gccggacctc    1740
agcgcgtgtg tgcatcagta agttaccaac agatgcacgg tttcagcgca gaacaactgc    1800
gtaataccac tcatctggtg tgggcgacgg gaggtggaat ggtgccggaa aagagatga     1860 atcaatatct ggcaaaaggc cgttaataac gtttcaacgc agcatcgcaa tccttttcct    1920
gggtgagcga tgctgccgat ggcgcagact taagatcccc ggtcttaccc gctataaccc    1980
cctccttttt                                                           1989
```

<210> SEQ ID NO 8
<211> LENGTH: 442
<212> TYPE: PRT
<213> ORGANISM: Escherichia coli

<400> SEQUENCE: 8

```
Met Glu Asn Ala Lys Met Asn Ser Leu Ile Ala Gln Tyr Pro Leu Val
1               5                  10                  15

Lys Asp Leu Val Ala Leu Lys Glu Thr Thr Trp Phe Asn Pro Gly Thr
            20                  25                  30

Thr Ser Leu Ala Glu Gly Leu Pro Tyr Val Gly Leu Thr Glu Gln Asp
        35                  40                  45

Val Gln Asp Ala His Ala Arg Leu Ser Arg Phe Ala Pro Tyr Leu Ala
    50                  55                  60

Lys Ala Phe Pro Glu Thr Ala Thr Gly Gly Ile Ile Glu Ser Glu
65                  70                  75                  80

Leu Val Ala Ile Pro Ala Met Gln Lys Arg Leu Glu Lys Glu Tyr Gln
                85                  90                  95

Gln Pro Ile Ser Gly Gln Leu Leu Lys Lys Asp Ser His Leu Pro
            100                 105                 110

Ile Ser Gly Ser Ile Lys Ala Arg Gly Gly Ile Tyr Glu Val Leu Ala
        115                 120                 125
```

-continued

```
His Ala Glu Lys Leu Ala Leu Glu Ala Gly Leu Leu Thr Leu Asp Asp
    130                 135                 140
Asp Tyr Ser Lys Leu Leu Ser Pro Glu Phe Lys Gln Phe Phe Ser Gln
145                 150                 155                 160
Tyr Ser Ile Ala Val Gly Ser Thr Gly Asn Leu Gly Leu Ser Ile Gly
                165                 170                 175
Ile Met Ser Ala Arg Ile Gly Phe Lys Val Thr Val His Met Ser Ala
            180                 185                 190
Asp Ala Arg Ala Trp Lys Lys Ala Lys Leu Arg Ser His Gly Val Thr
        195                 200                 205
Val Val Glu Tyr Glu Gln Asp Tyr Gly Val Ala Val Glu Glu Gly Arg
    210                 215                 220
Lys Ala Ala Gln Ser Asp Pro Asn Cys Phe Phe Ile Asp Asp Glu Asn
225                 230                 235                 240
Ser Arg Thr Leu Phe Leu Gly Tyr Ser Val Ala Gly Gln Arg Leu Lys
                245                 250                 255
Ala Gln Phe Ala Gln Gln Gly Arg Ile Val Asp Ala Asp Asn Pro Leu
            260                 265                 270
Phe Val Tyr Leu Pro Cys Gly Val Gly Gly Gly Pro Gly Gly Val Ala
        275                 280                 285
Phe Gly Leu Lys Leu Ala Phe Gly Asp His Val His Cys Phe Phe Ala
    290                 295                 300
Glu Pro Thr His Ser Pro Cys Met Leu Leu Gly Val His Thr Gly Leu
305                 310                 315                 320
His Asp Gln Ile Ser Val Gln Asp Ile Gly Ile Asp Asn Leu Thr Ala
                325                 330                 335
Ala Asp Gly Leu Ala Val Gly Arg Ala Ser Gly Phe Val Gly Arg Ala
            340                 345                 350
Met Glu Arg Leu Leu Asp Gly Phe Tyr Thr Leu Ser Asp Gln Thr Met
        355                 360                 365
Tyr Asp Met Leu Gly Trp Leu Ala Gln Glu Glu Gly Ile Arg Leu Glu
    370                 375                 380
Pro Ser Ala Leu Ala Gly Met Ala Gly Pro Gln Arg Val Cys Ala Ser
385                 390                 395                 400
Val Ser Tyr Gln Gln Met His Gly Phe Ser Ala Glu Gln Leu Arg Asn
                405                 410                 415
Thr Thr His Leu Val Trp Ala Thr Gly Gly Gly Met Val Pro Glu Glu
            420                 425                 430
Glu Met Asn Gln Tyr Leu Ala Lys Gly Arg
        435                 440
```